(12) United States Patent
Vesely

(10) Patent No.: US 8,486,138 B2
(45) Date of Patent: Jul. 16, 2013

(54) METHOD AND APPARATUS FOR PROSTHETIC VALVE REMOVAL

(75) Inventor: Ivan Vesely, Larkspur, CO (US)

(73) Assignee: ValveXchange Inc., Aurora, CO (US)

( * ) Notice: Subject to any disclaimer, the term of this patent is extended or adjusted under 35 U.S.C. 154(b) by 399 days.

(21) Appl. No.: 12/673,054

(22) PCT Filed: Aug. 19, 2008

(86) PCT No.: PCT/US2008/073565
§ 371 (c)(1),
(2), (4) Date: Feb. 11, 2010

(87) PCT Pub. No.: WO2009/026272
PCT Pub. Date: Feb. 26, 2009

(65) Prior Publication Data
US 2012/0010699 A1    Jan. 12, 2012

Related U.S. Application Data

(60) Provisional application No. 60/965,602, filed on Aug. 21, 2007.

(51) Int. Cl.
*A61F 2/24* (2006.01)
*A61B 17/32* (2006.01)

(52) U.S. Cl.
USPC .......................... 623/2.11; 606/170

(58) Field of Classification Search
USPC .......................... 623/2.11; 606/170
See application file for complete search history.

(56) References Cited

U.S. PATENT DOCUMENTS

| | | | | |
|---|---|---|---|---|
| 3,409,013 A | * | 11/1968 | Berry | 606/1 |
| 3,898,701 A | | 8/1975 | LaRussa | 3/1.5 |
| 4,056,854 A | | 11/1977 | Boretos et al. | 3/1.5 |
| 4,506,394 A | | 3/1985 | Bédard | 3/1.5 |
| 4,680,031 A | | 7/1987 | Alonso | 623/2 |
| 4,790,843 A | | 12/1988 | Carpentier et al. | 623/2 |
| 4,887,605 A | | 12/1989 | Angelsen et al. | 128/660.03 |
| 4,909,789 A | | 3/1990 | Taguchi et al. | 604/107 |
| 5,037,427 A | | 8/1991 | Harada et al. | 606/108 |
| 5,041,130 A | * | 8/1991 | Cosgrove et al. | 623/2.11 |
| 5,071,431 A | | 12/1991 | Sauter et al. | 623/2 |
| 5,087,264 A | | 2/1992 | Miller et al. | 606/159 |
| 5,113,846 A | | 5/1992 | Hiltebrandt et al. | 600/225 |
| 5,197,978 A | | 3/1993 | Hess | 623/1.18 |
| 5,234,443 A | | 8/1993 | Phan et al. | 606/148 |

(Continued)

FOREIGN PATENT DOCUMENTS

WO       99/33414       7/1999

OTHER PUBLICATIONS

International Search Report for International Application No. PCT/US2008/073565, Nov. 3, 2008.

(Continued)

*Primary Examiner* — Darwin Erezo
*Assistant Examiner* — Shaun L David
(74) *Attorney, Agent, or Firm* — Kusner & Jaffe

(57) ABSTRACT

A method and apparatus for facilitating transapical removal of a prosthetic heart valve, i.e., percutaneously implantable valve (PIV), without open-heart surgery. The apparatus includes a holding tool for holding the PIV, a cutting tool for separating the PrV from fibrotic tissue accumulating around the PIV, and a removal tool for extracting the PIV from the heart.

20 Claims, 17 Drawing Sheets

U.S. PATENT DOCUMENTS

| | | | | |
|---|---|---|---|---|
| 5,312,360 | A | 5/1994 | Behl | 604/164 |
| 5,336,230 | A | 8/1994 | Leichtling et al. | 606/148 |
| 5,411,552 | A | 5/1995 | Andersen et al. | 623/2 |
| 5,474,563 | A * | 12/1995 | Myler et al. | 606/108 |
| 5,476,510 | A | 12/1995 | Eberhardt et al. | 623/2.11 |
| 5,545,214 | A | 8/1996 | Stevens | 623/2 |
| 5,554,185 | A | 9/1996 | Block et al. | 623/2 |
| 5,571,174 | A | 11/1996 | Love et al. | 623/2 |
| 5,584,803 | A | 12/1996 | Stevens et al. | 604/4 |
| 5,593,424 | A | 1/1997 | Northrup, III | 606/232 |
| 5,607,446 | A | 3/1997 | Beehler et al. | 606/198 |
| 5,662,676 | A | 9/1997 | Koninckx | 606/198 |
| 5,667,525 | A | 9/1997 | Ishibashi | 606/206 |
| 5,718,725 | A | 2/1998 | Sterman et al. | 623/2 |
| 5,807,405 | A | 9/1998 | Vanney et al. | 623/112 |
| 5,814,054 | A | 9/1998 | Kortenbach et al. | 606/139 |
| 5,840,081 | A | 11/1998 | Andersen et al. | 623/1.11 |
| 5,843,103 | A | 12/1998 | Wulfman | 606/159 |
| 5,843,181 | A | 12/1998 | Jaffe et al. | 623/2 |
| 5,855,601 | A | 1/1999 | Bessler et al. | 623/2 |
| 5,910,144 | A | 6/1999 | Hayashi | 606/108 |
| 5,910,170 | A | 6/1999 | Reimink et al. | 623/2 |
| 5,957,949 | A | 9/1999 | Leonhardt et al. | 606/194 |
| 6,004,328 | A | 12/1999 | Solar | 606/108 |
| 6,071,263 | A | 6/2000 | Kirkman | 604/104 |
| 6,106,550 | A | 8/2000 | Magovern et al. | 623/2.38 |
| 6,156,055 | A | 12/2000 | Ravenscroft | 606/206 |
| 6,168,614 | B1 | 1/2001 | Andersen et al. | 623/1 |
| 6,168,616 | B1 | 1/2001 | Brown, III | 623/1.11 |
| 6,187,016 | B1 | 2/2001 | Hedges et al. | 606/108 |
| 6,197,054 | B1 | 3/2001 | Hamblin, Jr. et al. | 623/2.38 |
| 6,217,585 | B1 | 4/2001 | Houser et al. | 606/108 |
| 6,312,465 | B1 | 11/2001 | Griffin et al. | 623/2.38 |
| 6,383,205 | B1 | 5/2002 | Samson et al. | 606/200 |
| 6,508,827 | B1 | 1/2003 | Manhes | 606/205 |
| 6,530,952 | B2 | 3/2003 | Vesely | 623/2.18 |
| 6,579,305 | B1 | 6/2003 | Lashinski | 623/1.11 |
| 6,629,534 | B1 * | 10/2003 | St. Goar et al. | 128/898 |
| 6,769,434 | B2 | 8/2004 | Liddicoat et al. | 128/898 |
| 6,821,297 | B2 | 11/2004 | Snyders | 623/2.18 |
| 6,893,459 | B1 | 5/2005 | Macoviak | 623/2.11 |
| 7,041,132 | B2 | 5/2006 | Quijano et al. | 623/2.11 |
| 7,063,707 | B2 | 6/2006 | Bose et al. | 606/127 |
| 7,201,761 | B2 | 4/2007 | Woolfson et al. | 606/170 |
| 7,323,003 | B2 | 1/2008 | Lowe | 606/200 |
| 7,329,279 | B2 | 2/2008 | Haug et al. | 623/2.11 |
| 7,381,219 | B2 * | 6/2008 | Salahieh et al. | 623/2.11 |
| 7,544,206 | B2 | 6/2009 | Cohn | 623/2.11 |
| 7,815,676 | B2 * | 10/2010 | Greenberg | 623/2.11 |
| 7,824,442 | B2 | 11/2010 | Salahieh et al. | 623/2.11 |
| 7,824,443 | B2 | 11/2010 | Salahieh et al. | 623/2.11 |
| 7,959,666 | B2 | 6/2011 | Salahieh et al. | 623/1.26 |
| 7,959,672 | B2 | 6/2011 | Salahieh et al. | 623/2.17 |
| 7,993,362 | B2 | 8/2011 | Lowe et al. | 606/200 |
| 8,025,668 | B2 | 9/2011 | McCartney | 606/106 |
| 2001/0002445 | A1 | 5/2001 | Vesely | 623/2.11 |
| 2002/0128702 | A1 | 9/2002 | Menz et al. | 623/1.12 |
| 2002/0173811 | A1 * | 11/2002 | Tu et al. | 606/159 |
| 2004/0039442 | A1 | 2/2004 | St. Goar et al. | 623/2.36 |
| 2004/0147939 | A1 | 7/2004 | Rabkin et al. | 606/108 |
| 2005/0137692 | A1 | 6/2005 | Haug et al. | 623/2.11 |
| 2005/0165479 | A1 | 7/2005 | Drews et al. | 623/2.38 |
| 2005/0203614 | A1 | 9/2005 | Forster et al. | 623/2.11 |
| 2005/0216079 | A1 | 9/2005 | MaCoviak | 623/2.38 |
| 2005/0228495 | A1 | 10/2005 | Macoviak | 623/2.18 |
| 2006/0287717 | A1 | 12/2006 | Rowe et al. | 623/2.11 |
| 2007/0027535 | A1 | 2/2007 | Purdy et al. | 623/2.18 |
| 2007/0088431 | A1 * | 4/2007 | Bourang et al. | 623/2.11 |
| 2007/0260305 | A1 * | 11/2007 | Drews et al. | 623/2.11 |
| 2008/0004696 | A1 | 1/2008 | Vesely | 623/2.1 |
| 2008/0033545 | A1 | 2/2008 | Bergin et al. | 623/2.11 |
| 2008/0065011 | A1 * | 3/2008 | Marchand et al. | 604/103.02 |
| 2008/0071367 | A1 | 3/2008 | Bergin et al. | 623/2.11 |
| 2008/0228254 | A1 | 9/2008 | Ryan | 623/1.2 |
| 2010/0004739 | A1 | 1/2010 | Vesely | 623/2.11 |
| 2011/0257735 | A1 | 10/2011 | Salahieh et al. | 623/2.11 |
| 2012/0016469 | A1 | 1/2012 | Salahieh et al. | 623/2.11 |
| 2012/0041549 | A1 | 2/2012 | Salahieh et al. | 623/2.11 |
| 2012/0046740 | A1 | 2/2012 | Paul et al. | 623/2.11 |
| 2012/0053683 | A1 | 3/2012 | Salahieh et al. | 623/2.11 |
| 2012/0078354 | A1 | 3/2012 | Cohn | 623/2.11 |

OTHER PUBLICATIONS

International Search Report for International Application No. PCT/US2009/56633, Nov. 13, 2009.

* cited by examiner

METHOD AND APPARATUS FOR PROSTHETIC VALVE REMOVAL

RELATED APPLICATIONS

This application claims the benefit of U.S. Provisional Application No. 60/965,602, filed Aug. 21, 2007, which is fully incorporated herein by reference.

FIELD OF INVENTION

The present invention relates generally to removal of a previously implanted cardiovascular valve, and more particularly to method and apparatus for facilitating removal of a percutaneously implantable valve (PIV) without open-heart surgery.

BACKGROUND OF THE INVENTION

The demographics of patients suffering valvular disease are broad and the treatment modalities for each are complex. Historically, patients younger than 65 years of age have received mechanical valves, while older patients have received bioprosthetic valves. A new demographic of prosthetic valve recipients has emerged recently, namely, the old, sick, inoperable patient who previously would not be a candidate for surgical implantation of a prosthetic valve. These patients are now candidates for a relatively new type of prosthetic valve, i.e., the percutaneously implantable valve (PIV). The PIV is configured like an endovascular stent, except with a tissue valve sewn in the lumen. Like the endovascular stent, the PIV is balloon expandable or self-expanding, and is delivered by way of a catheter to the operative site, where it is deployed and the delivery system removed. The principal advantage of a PIV is that it avoids open-heart surgery. The old, sick patients who would otherwise not survive open heart surgery, can now benefit from the PIV.

Because of a number of design constraints, PIV's are expected to be less durable and are likely to wear out sooner than conventional, surgically implantable valves. Although PIVs are intended for the old, sick patients who have a relatively short life expectancy, there may be instances in which the patient outlives the functional lifespan of the PIV. Therefore, when the PIV ceases to function, it must be replaced.

One potential solution to replacement of a PIV is to insert a new PIV inside the pre-existing PIV. In the field of interventional cardiology, this replacement process is referred to as "restenting." Restenting a PIV invariably leads to a reduction of effective orifice area of the prosthetic valve, since the old metal cage and worn-out calcified leaflets remain in place and the new PIV is smaller than the pre-existing PIV in order to allow it to be inserted into the remaining lumen. Depending on the original size of the first PIV, and the degree of calcification and obstruction, restenting with another PIV may not lead to an effective orifice area that is compatible with good cardiac function.

As indicated above, there may be instances where an old, worn-out PIV will need to be replaced. Currently, the only means of replacing an old, worn-out, fibrosed PIV is through open heart surgery. Since the patient likely received the PIV because they were not a candidate for open-heart surgery and implantation of a conventional bioprosthesis, the patient is unlikely to be a candidate for open heart surgery to replace a worn or failed PIV. Therefore, non-surgical removal of the existing PIV is a preferred option.

In view of the issues discussed above, the concept of a system for the removal of an old and/or failed PIV becomes very desirable. The present invention provides a method and apparatus for non-surgical removal of a PIV, and includes a set of tools comprising a valve holding tool, a cutting tool and a valve removal tool that facilitate removal of the PIV through the apex of the heart.

SUMMARY OF THE INVENTION

In accordance with the present invention, there is provided a holding tool for facilitating removal of an implantable cardiovascular valve, the holding tool comprising: a first sliding member; a second sliding member moveable relative to the first sliding member; and a first articulating joint member connected to the first and second sliding members, said articulating joint member moveable between a collapsed position and an expanded position, wherein movement of the second sliding member relative to the first sliding member moves the first articulating joint member between the collapsed and expanded positions.

In accordance with another aspect of the present invention, there is provided a cutting tool for facilitating removal of an implantable cardiovascular valve, the cutting tool comprising: a shaft having a longitudinal axis; and a cutting arm extending from the hollow shaft, wherein said cutting arm includes cutting means for cutting tissue.

In accordance with still another aspect of the present invention, there is provided a valve removal tool for facilitating removal of an implantable cardiovascular valve from a heart, the valve removal tool comprising: a body; capture means mounted to the body and moveable between a collapsed position and an expanded position, for capturing the implantable cardiovascular valve; and an actuator for actuating movement of the capture means between the collapsed and expanded positions.

In accordance with yet another aspect of the present invention, there is provided a method for removing an implantable cardiovascular valve from a heart, the method comprising: holding the cardiovascular valve using a valve holding tool; separating the cardiovascular valve from fibrotic tissue that accumulates adjacent to the cardiovascular valve; and removing the cardiovascular valve from the heart using a valve removal tool, said step of removing including: capturing the cardiovascular valve, and extracting the cardiovascular valve from the heart.

An advantage of the present invention is the provision of apparatus for facilitating removal of a percutaneously implantable valve (PIV) from a heart.

Another advantage of the present invention is the provision of a valve holding tool, a cutting tool and a valve removal tool for facilitating removal of a percutaneously implantable valve (PIV) from a heart.

A still further advantage of the present invention is the provision of a method for facilitating removal of a percutaneously implantable valve (PIV) from a heart.

These and other advantages will become apparent from the following description taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE INVENTION

Figure 1:
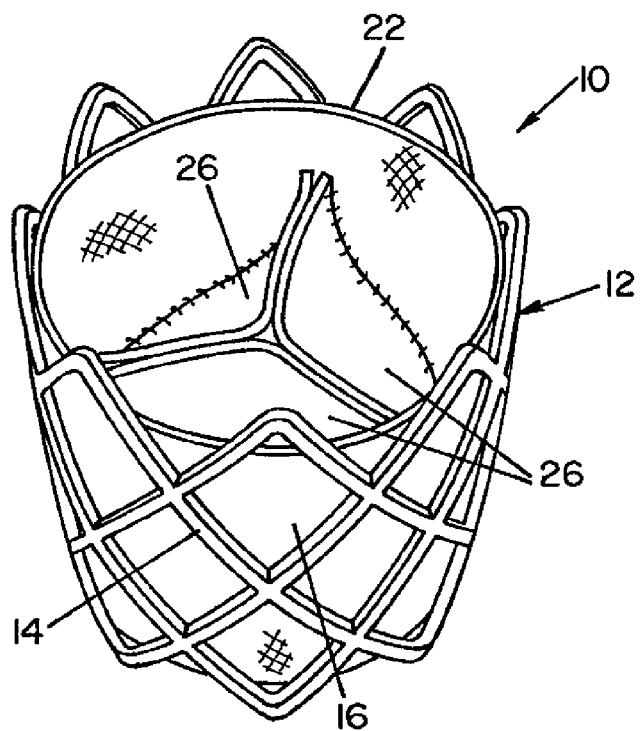
FIG. 1 is a perspective view of a typical PIV shown schematically.
Figure 2:
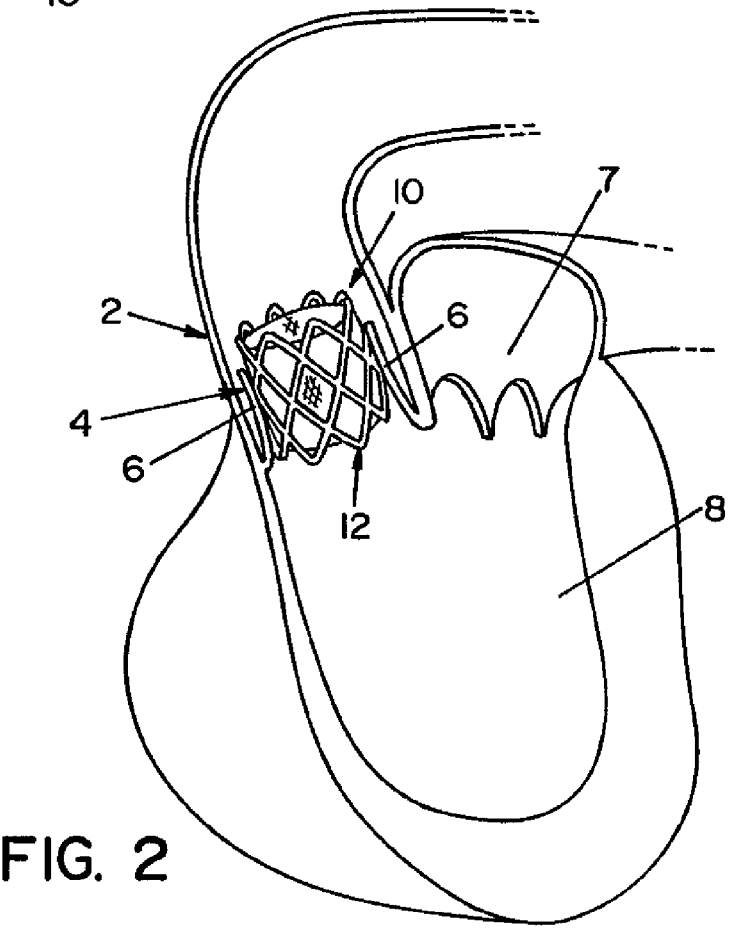
FIG. 2 is a schematic diagram showing a PIV deployed inside a native aortic valve.

Referring now to the drawings wherein the showings are for the purposes of illustrating an embodiment of the invention only and not for the purposes of limiting same, FIG. 1 shows a typical PIV 10 that may be removed in connection with the present invention. PIV 10 is generally comprised of a flexible, expandable, tubular member 12, a tubular liner 22 and a plurality of leaflets 26. As illustrated, tubular member 12 is a mesh cylinder or metal cage formed of intersecting wire sections 14 that define a plurality of openings 16. Tubular member 12 is radially expandable to contact with tissue, as shown in FIG. 2. Liner 22 is formed of tissue or a fabric, such as a woven polyester (e.g., polyethylene terepthalate). Leaflets 26 are typically formed from pericardial tissue, such as bovine or equine pericardium. Alternatively, leaflets 26 may be formed of synthetic materials. It should be appreciated that PIV 10 shown in FIG. 1 is exemplary of a typical PIV, and is not intended in any way to limit the scope of the present invention. In this respect, it is contemplated that the method and apparatus of the present invention are suitable for use in connection with implantable cardiovascular valves of a wide variety of configurations.

Figure 3:
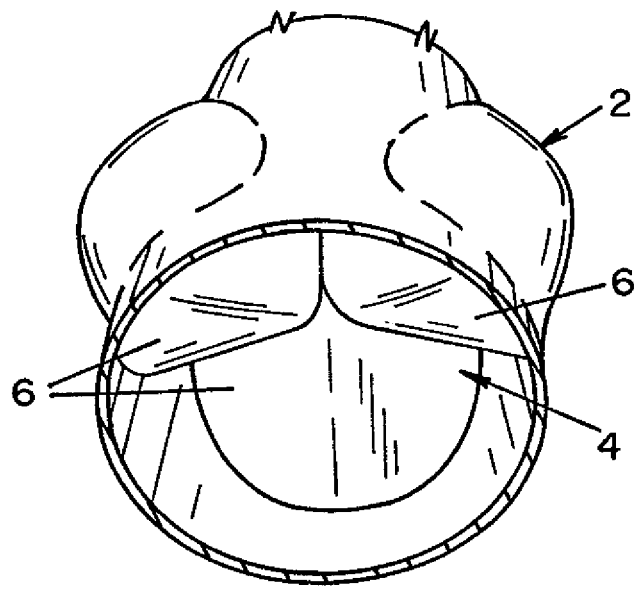
FIG. 3 is a bottom perspective view (inflow aspect) of an aortic root of a heart, including native aortic valve leaflets.
Figure 4:
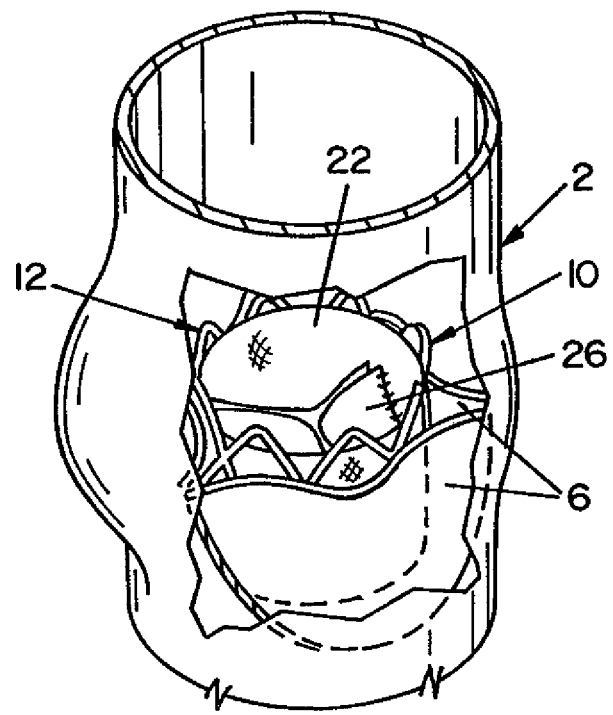
FIG. 4 is a partial cut-away view of an aortic root of a heart with a PIV inserted between the native aortic valve leaflets.

FIG. 2 shows a portion of a heart, including aortic root 2, mitral valve 7 and left ventricle 8. PIV 10 of FIG. 1 is shown deployed inside a native aortic valve 4, wherein PIV 10 is inserted between native valve leaflets 6. FIG. 3 is a bottom perspective view (inflow aspect) of aortic root 2 without PIV 10. In FIG. 4, aortic root 2 is shown in detail with PIV 10 installed between aortic valve leaflets 6. It should be noted that fibrotic tissue (not shown) will accumulate around PIV 10 during the years following implantation.

Figure 5:
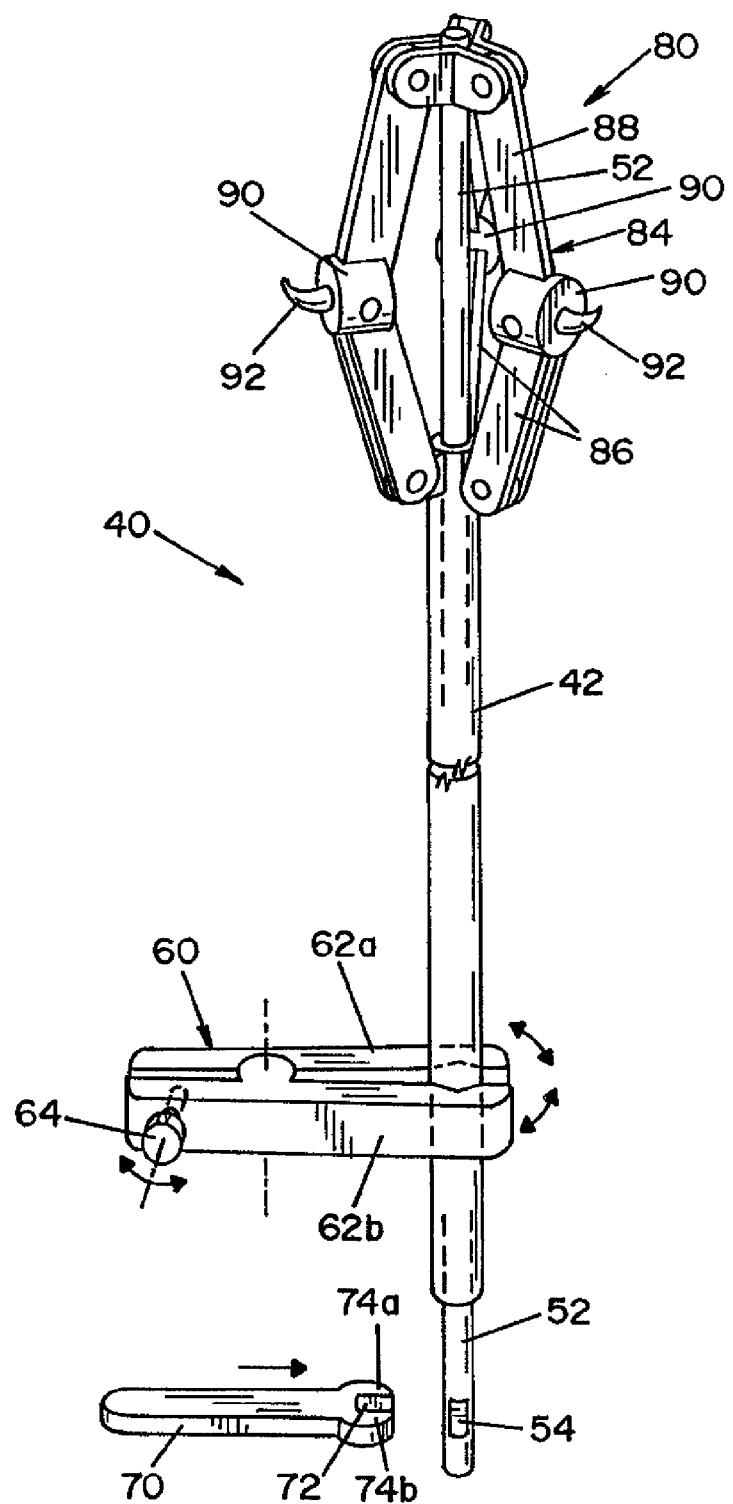
FIG. 5 is a perspective view of a valve holding tool of the present invention, according to a first embodiment, wherein the valve holding tool is shown in a collapsed position.
Figure 6A:
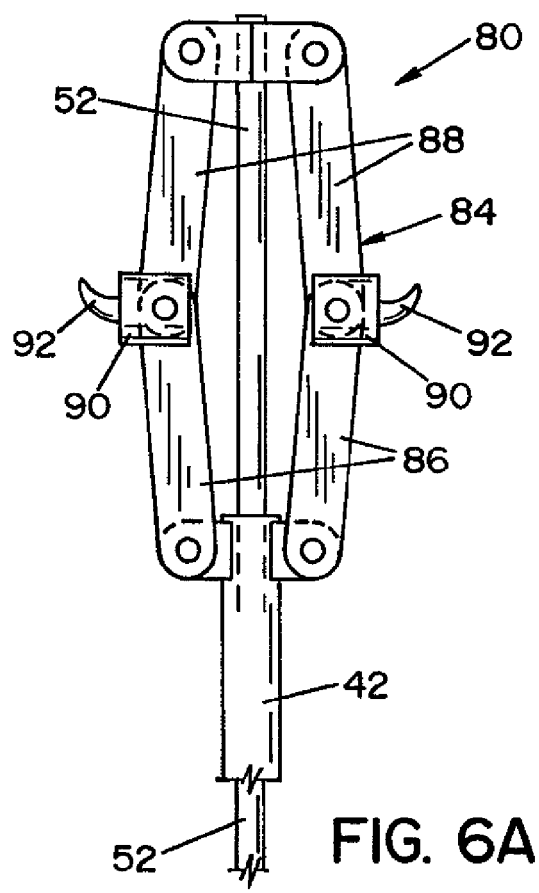
FIG. 6A is a plan view of the articulating joint member of the valve holding tool of FIG. 5, wherein the valve holding tool is shown in a collapsed position.
Figure 6B:
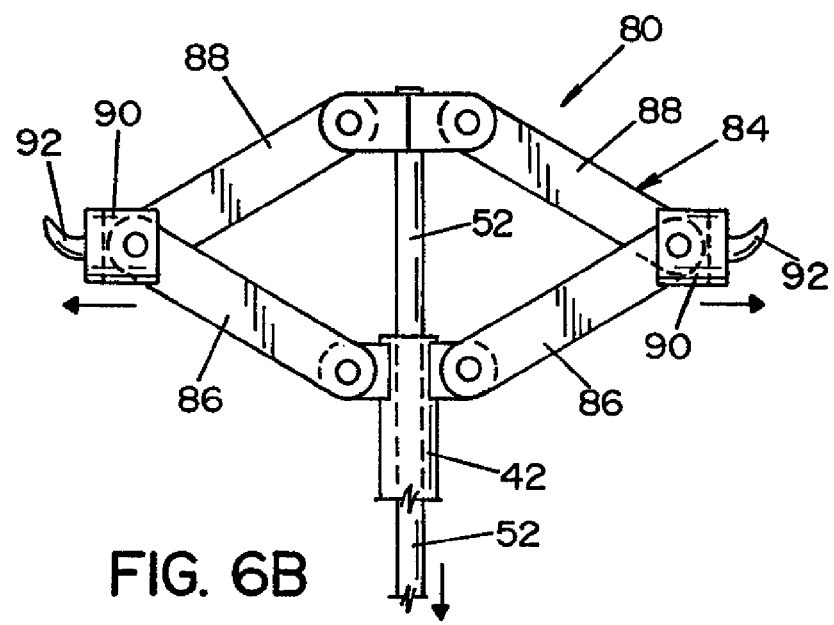
FIG. 6B is a plan view of the articulating joint member of the valve holding tool of FIG. 5, wherein the valve holding tool is shown in an expanded position.

Referring now to FIGS. 5, 6A and 6B, there is shown a valve holding tool 40 of the present invention, according to a first embodiment. Holding tool 40 is generally comprised of a first sliding member in the form of an outer tubular body 42, a second sliding member in the form of an inner rod 52, and an articulating joint member 80 that is pivotally connected with tubular body 42 and inner rod 52. Tubular body 42 and inner rod 52 form a stem portion of holding tool 40. Tubular body 42 defines a cylindrical recess dimensioned to receive rod 52 and has an outer surface dimensioned to receive a detachable handle 60. One end of rod 52 is connected with tubular body 42 by articulating joint member 80, while the other end of rod 52 is adapted to receive a detachable handle 70.

With reference to FIG. 5, detachable handles 60 and 70 facilitate longitudinally movement of rod 52 relative to tubular body 42 for moving articulating joint member 80 between collapsed and expanded positions, as will be described below. Notches 54 may be respectively formed in tubular body 42 and rod 52 to provide flat surfaces suitable for secure attachment of handles 60 and 70.

Handle 60 includes a pair of pivotally connected arms 62a and 62b. In the illustrated embodiment, a set screw 64 is provided that moves arms 62a and 62b towards each other when tightened, and moves arms 62a and 62b away from each other when loosened. Accordingly, arms 62a and 62b are moved towards each other to capture tubular body 42 between arms 62a and 62b, and thereby detachably engage handle 60 with tubular body 42. Handle 70 includes a recess 72 that defines a pair of fingers 74a, 74b. Rod 52 is captured between fingers 74a and 74b to attach handle 70 to rod 52.

It should be appreciated that handles 60 and 70 are exemplary embodiments of suitable detachable handles for use in connection with holding tool 40, and that the handles may take other suitable forms. Moreover, handle 60 may be substituted for handle 70, and vice versa. Handles 60 and 70 are configured to be detachable to allow other tools (e.g., cutting and valve removal tools) to conveniently slide over the stem portion of holding tool 40, as will be described below.

Articulating joint member 80 is comprised of a plurality of articulating legs 84. Each articulating leg 84 includes first and second leg sections 86 and 88 that are pivotally connected to each other at a hub member 90. First leg section 86 is pivotally connected at one end with tubular body 42 and second leg section 88 is pivotally connected at one end with rod 52. Each hub member 90 includes a projection 92 dimensioned to engage with tubular member 12 of PIV 10. In the illustrated embodiment, projection 92 takes the form of an outward extending hook 92. It is contemplated that projection 92 may take other suitable forms.

As rod 52 is moved relative to tubular body 42, articulating joint member 80 moves between a collapsed position (FIGS. 5 and 6A) and an expanded position (FIG. 6B). In the expanded position, projections 92 can grasp wire sections 14 of tubular member 12 and/or hook onto liner 22, thereby engaging holding tool 40 with PIV 10.

It should be appreciated that the angular geometry of articulating joint member 80 allows projections 92 to exert significant outward force against tubular member 12 and/or liner 22 of PIV 10, when articulating joint member 80 is moved to the expanded position. Accordingly, a surgeon removing PIV 10 can conveniently grasp holding tool 40 with one hand, thereby stabilizing the heart and PIV 10, while manipulating cutting tool 120 around PIV 10, as will be described below.

Figure 7:
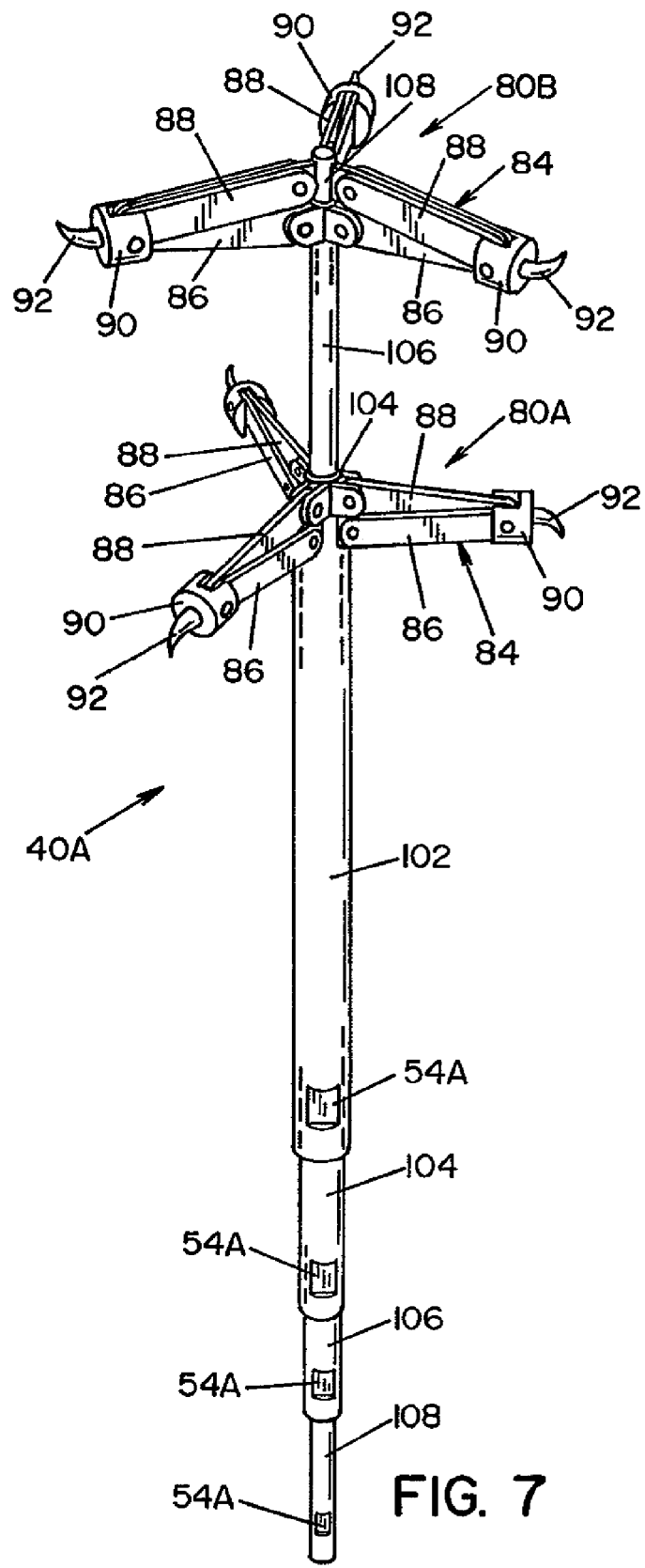
FIG. 7 is a perspective view of a valve holding tool of the present invention, according to a second embodiment, wherein the valve holding tool is shown in an expanded position.
Figure 8:
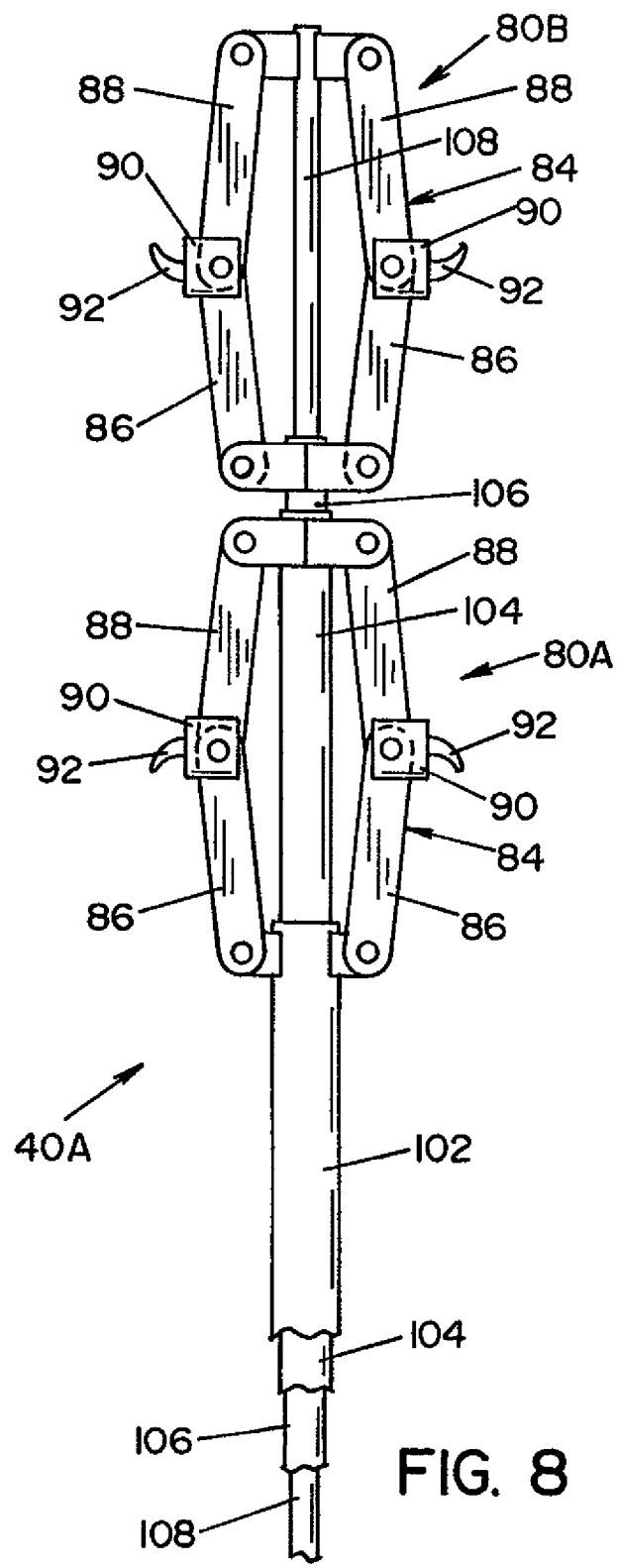
FIG. 8 is a plan view of the articulating joint member of the valve holding tool of FIG. 7, wherein the valve holding tool is shown in a collapsed position.

FIGS. 7 and 8 illustrate a holding tool 40A of the present invention, according to a second embodiment. Holding tool 40A includes a first sliding member in the form of an outer tubular body 102, a second sliding member in the form of an inner tubular body 104, a third sliding member in the form of an inner tubular body 106, a fourth sliding member in the form of an inner rod 108, and a pair of articulating joint members 80A and 80B. In this embodiment, outer tubular body 102, inner tubular body 104, inner tubular body 106, and inner rod 108 form a stem portion of holding tool 40A, wherein inner tubular body 104 extends through outer tubular body 102, inner tubular body 106 extends through inner tubular body 104, and inner rod 108 extends through inner tubular body 106.

Articulating joint members 80A and 80B are essentially the same as articulating joint member 80 described above. Thus, like components are given the same reference numbers. Articulating joint member 80A is pivotally connected with tubular body 102 and inner tubular body 104. Similarly, articulating joint member 80B is pivotally connected with inner tubular body 106 and inner rod 108. Notches 54A dimensioned to receive detachable handles are respectively formed in outer tubular body 102, inner tubular body 104, inner tubular body 106, and inner rod 108. The detachable handles may take the form of handles 60 or 70 described above.

Figure 9:
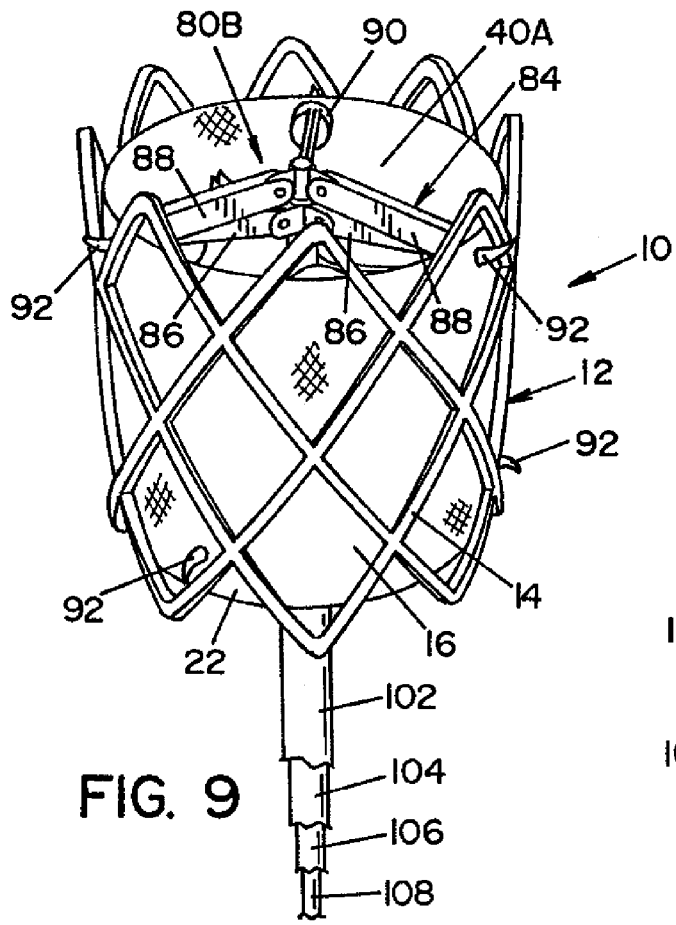
FIG. 9 is a perspective view of the valve holding tool of FIG. 7 in the expanded position and engaged with a PIV.

As inner tubular body 104 is moved relative to tubular body 102, articulating joint member 80A moves between a collapsed position (FIG. 8) and an expanded position (FIG. 7). Likewise, as inner rod 108 is moved relative to inner tubular body 106, articulating joint member 80B moves between a collapsed position (FIG. 8) and an expanded position (FIG. 7). In the expanded position, projections 92 of articulating joint members 80A, 80B grasp wire sections 14 of tubular member 12 and/or hook onto liner 22, thereby engaging holding tool 40A with PIV 10. FIG. 9 illustrates holding tool 40A in engagement with PIV 10.

It should be appreciated that holding tools 40, 40A not only serve the function of holding PIV 10, but also act as a guide to locate the cutting and valve removal tools relative to PIV 10.

Figure 10:
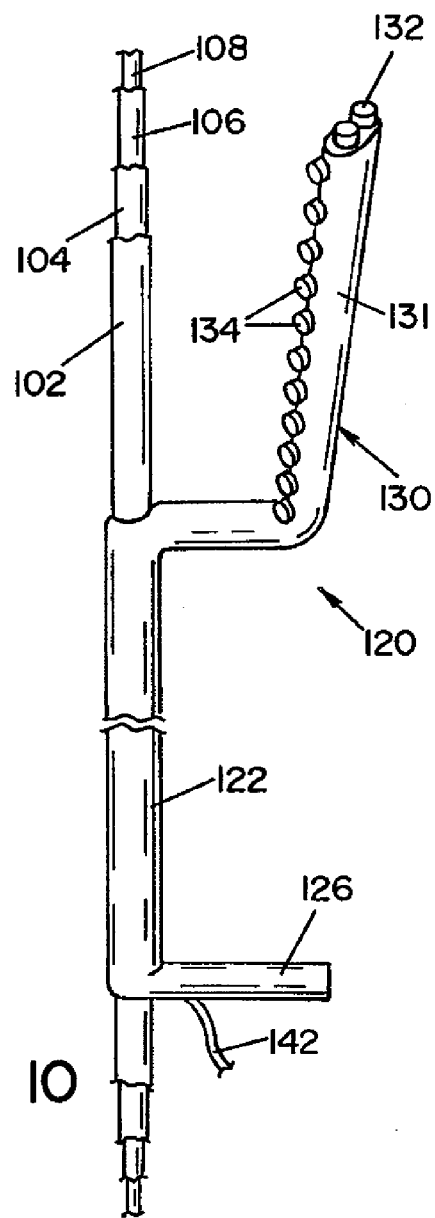
FIG. 10 is a perspective view of a cutting tool of the present invention, wherein the cutting tool is shown mounted over a stem portion of the valve holding tool shown in FIG. 7.
Figure 11:
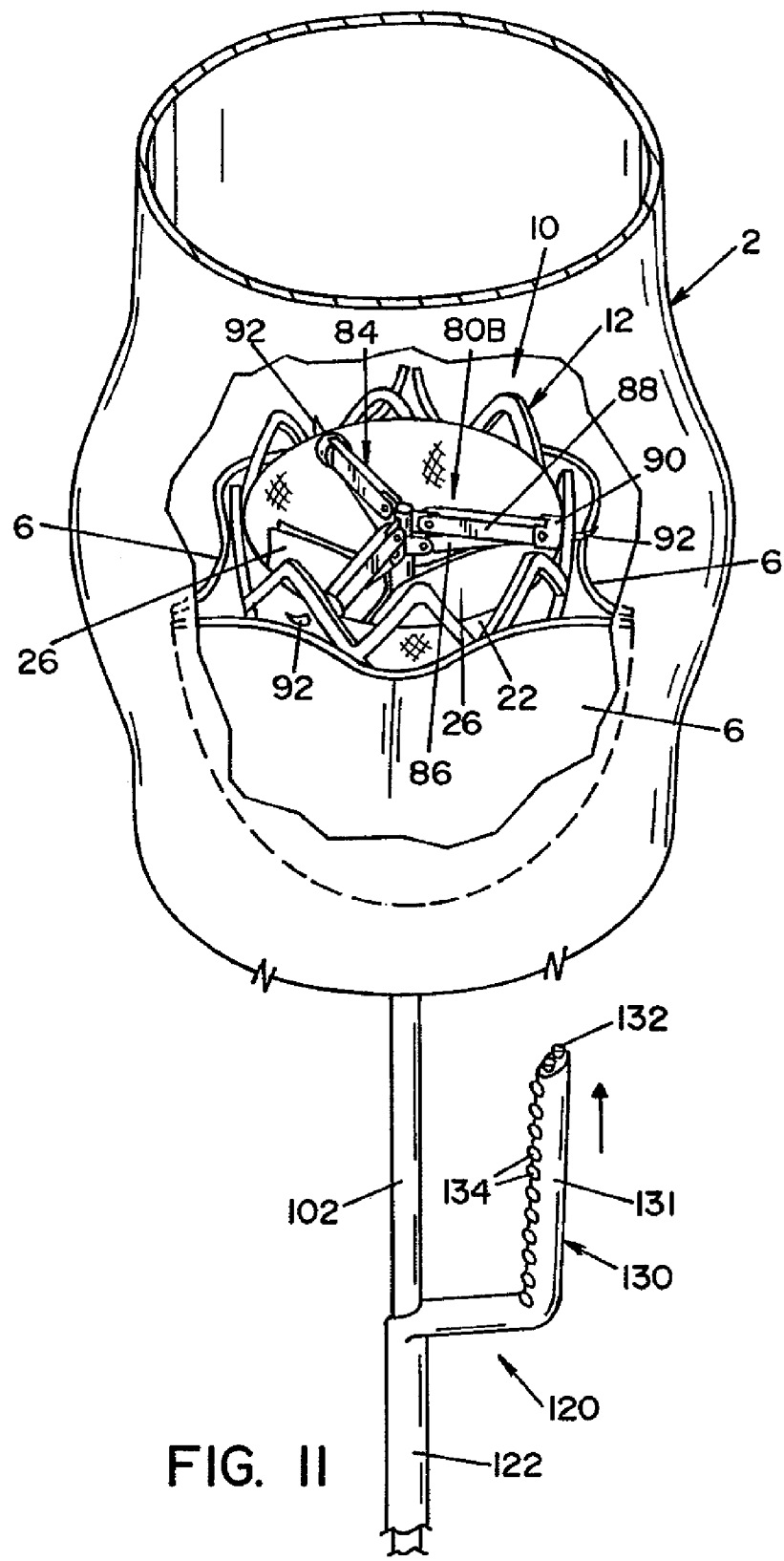
FIG. 11 is a perspective view showing the valve holding tool of FIG. 7 engaged with a PIV located inside an aortic valve, and a cutting tool mounted over the stem portion of the valve holding tool.

Referring now to FIGS. 10 and 11, there is shown a cutting tool 120 according to the present invention. In the figures, cutting tool 120 is shown mounted over the stem portion of holding tool 40A. It should be appreciated that holding tool 40 may be substituted for holding tool 40A. Cutting tool 120 is generally comprised of a hollow shaft 122, a handle portion 126 extending from a first end of shaft 122, and an L-shaped cutting arm 130 extending from a second end of shaft 122.

Shaft 122 includes a cylindrical recess dimensioned to receive the stem portion of holding tool 40A. In this respect, shaft 122 is slidable over the stem portion of holding tool 40A, when all handles are detached therefrom. Handle portion 126 provides a surface for gripping and maneuvering cutting tool 120.

Figure 13:
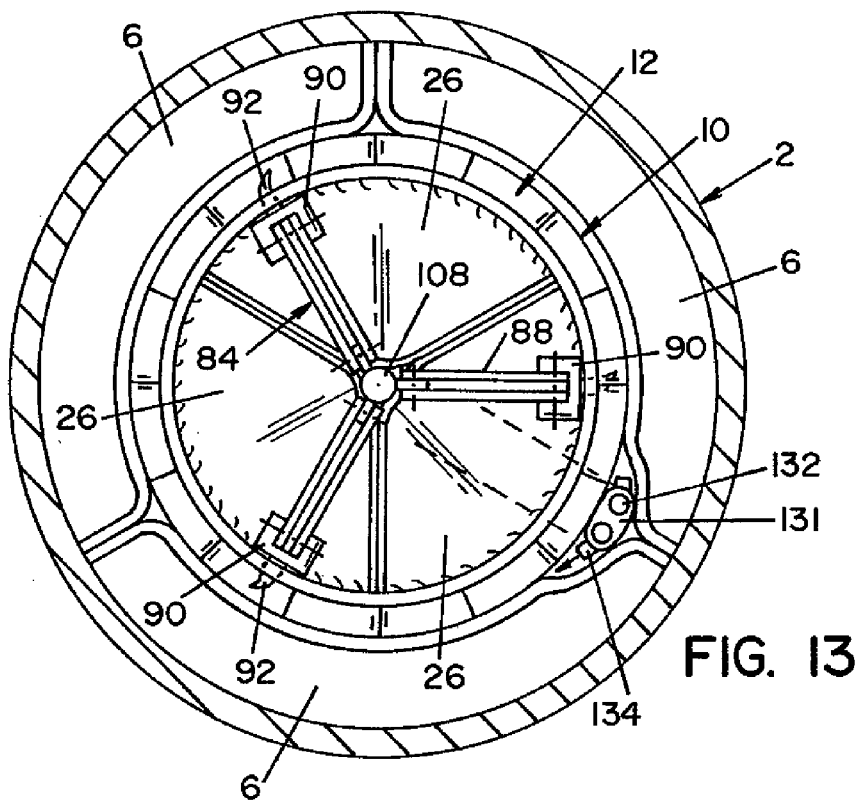
FIG. 13 is a top plan view of the aortic valve shown in FIG. 12, wherein the cutting arm of the cutting tool is located adjacent to the PIV, the cutting tool burning a channel adjacent to the metal cage of the PIV.
Figure 14:
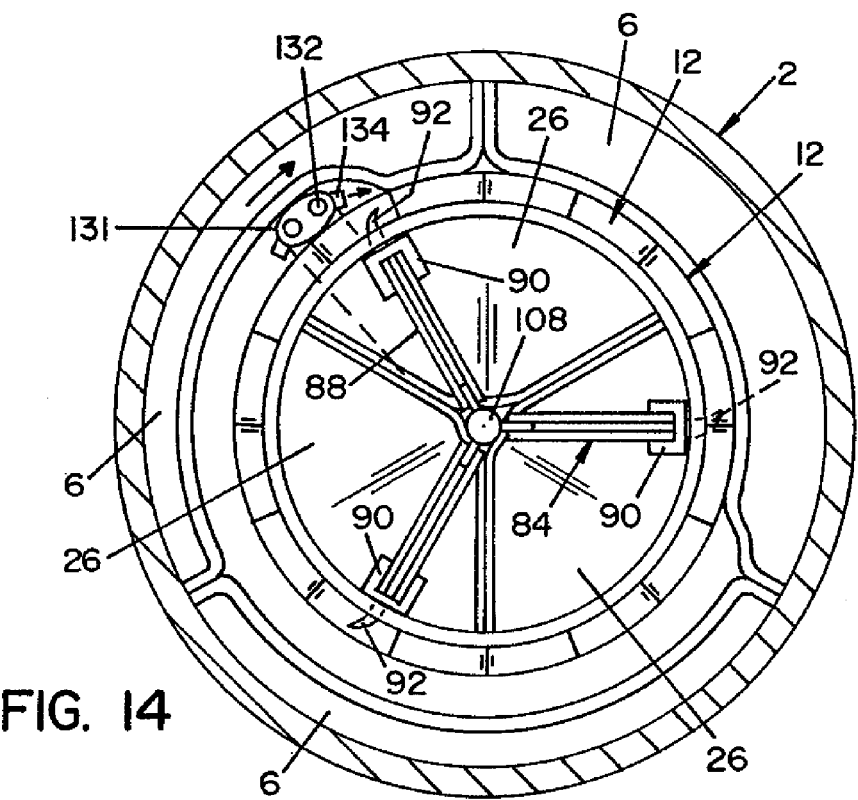
FIG. 14 is a top plan view of the aortic valve shown in FIG. 12, wherein the cutting arm of the cutting tool is located adjacent to the PIV, the cutting tool burning a generally annular-shaped recess along the periphery of the PIV metal cage.

Arm 130 includes an elongated portion 131 that is generally parallel to the longitudinal axis of shaft 122. A plurality of axially-mounted fiber optic guides 132 and a plurality of transverse-mounted fiber optic guides 134 are mounted to elongated portion 131 of arm 130. Internal channels (not shown), formed within handle portion 126, shaft 122 and arm 130, are dimensioned to receive fiber optic cable 142. Fiber optic cable 142 connects fiber optic guides 132, 134 to a source of laser energy (not shown). Accordingly, laser energy is transmitted to fiber optic guides 132, 134 via fiber optic cable 142. Fiber optic guides 132 emit laser beams in a direction generally parallel to the longitudinal axis of shaft 122, while fiber optic guides 134 emit laser beams in a direction transverse to the longitudinal axis of shaft 122. Accordingly, fiber optic guides 132 are appropriately positioned to cut (i.e., burn) a channel adjacent to PIV 10 (FIGS. 12 and 13), and fiber optic guides 134 are appropriately positioned to cut (i.e., burn) a generally annular recess around the periphery of PIV 10 (FIG. 14).

In FIGS. 10-14, cutting tool 120 is shown in conjunction with holding tool 40A for the purpose of illustrating operation of cutting tool 120. However, it should be appreciated that holding tool 40 may be substituted for holding tool 40A.

It is contemplated that other suitable cutting means may be substituted for the laser-based cutting means comprised of fiber optic guides, fiber optic cable and a laser energy source. For example, the cutting tool may include cutting means in the form of a mechanical cutting device, such as a conventional mechanical oscillating cutting blade, or an electrosurgical cutting device. A conventional electrosurgical cutting device includes electrode(s) for applying a high frequency, high voltage to tissue. It is further contemplated that the cutting tool may include a combination of different types of cutting means.

Figure 12:
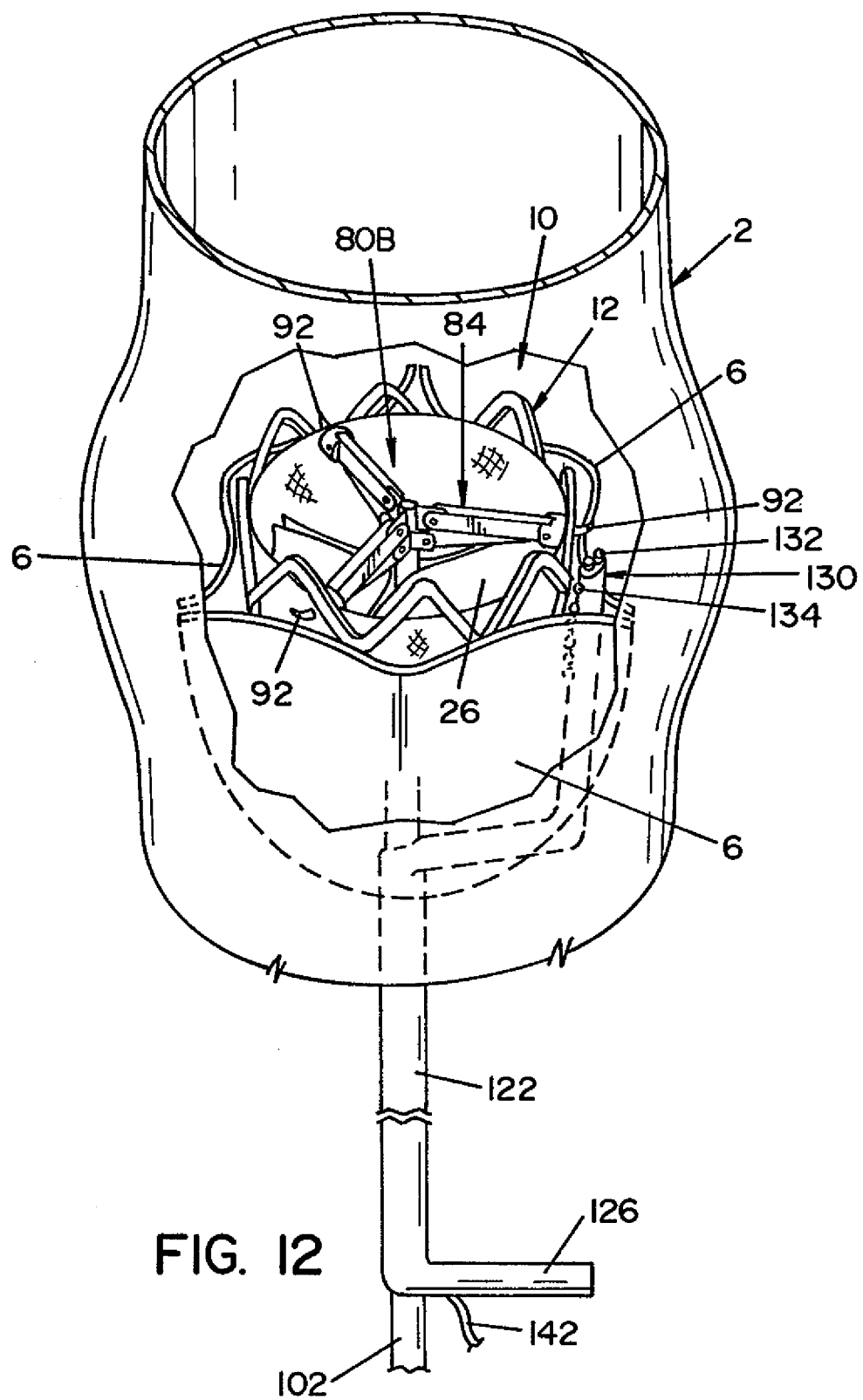
FIG. 12 is a perspective view showing the valve holding tool of FIG. 7 engaged with a PIV located inside an aortic valve, and a cutting tool mounted over the stem portion of the valve holding tool, the cutting tool having a cutting arm located between the PIV and the native aortic valve leaflets.

The operation of cutting tool 120 will now be described detail with reference to FIGS. 11-14. After holding tool 40A is properly engaged with PIV 10 (as described above), handles 60 and 70 are removed from holding tool 40A. Cutting tool 120 is then mounted over the stem portion of holding tool 40A, as shown in FIG. 11. Cutting tool 120 is slid along the stem portion while fiber optic guides 132 are energized to emit laser beams in an axial direction. Accordingly, a channel is burned adjacent to PIV 10, as shown in FIGS. 12 and 13. Thereafter, cutting tool 120 is rotated circumferentially while fiber optic guides 134 are energized to emit laser beams in a transverse direction. Accordingly, a generally annular recess is formed around the periphery of PIV 10, as shown in FIG. 14. Handle portion 126 is used to move and rotate cutting tool 120 relative to PIV 10. The cutting of the channel and a complete annular recess using cutting tool 120 is necessary to separate PIV 10 from fibrotic tissue that accumulates adjacent to PIV 10. After PIV 10 is separated from fibrotic tissue, cutting tool 120 is removed by dismounting it from the stem portion of holding tool 40A. PIV 10 is stabilized by grasping the stem portion of holding tool 40. Handles 60, 70 may be re-attached to the stem portion after mounting cutting tool 120.

Figure 15:
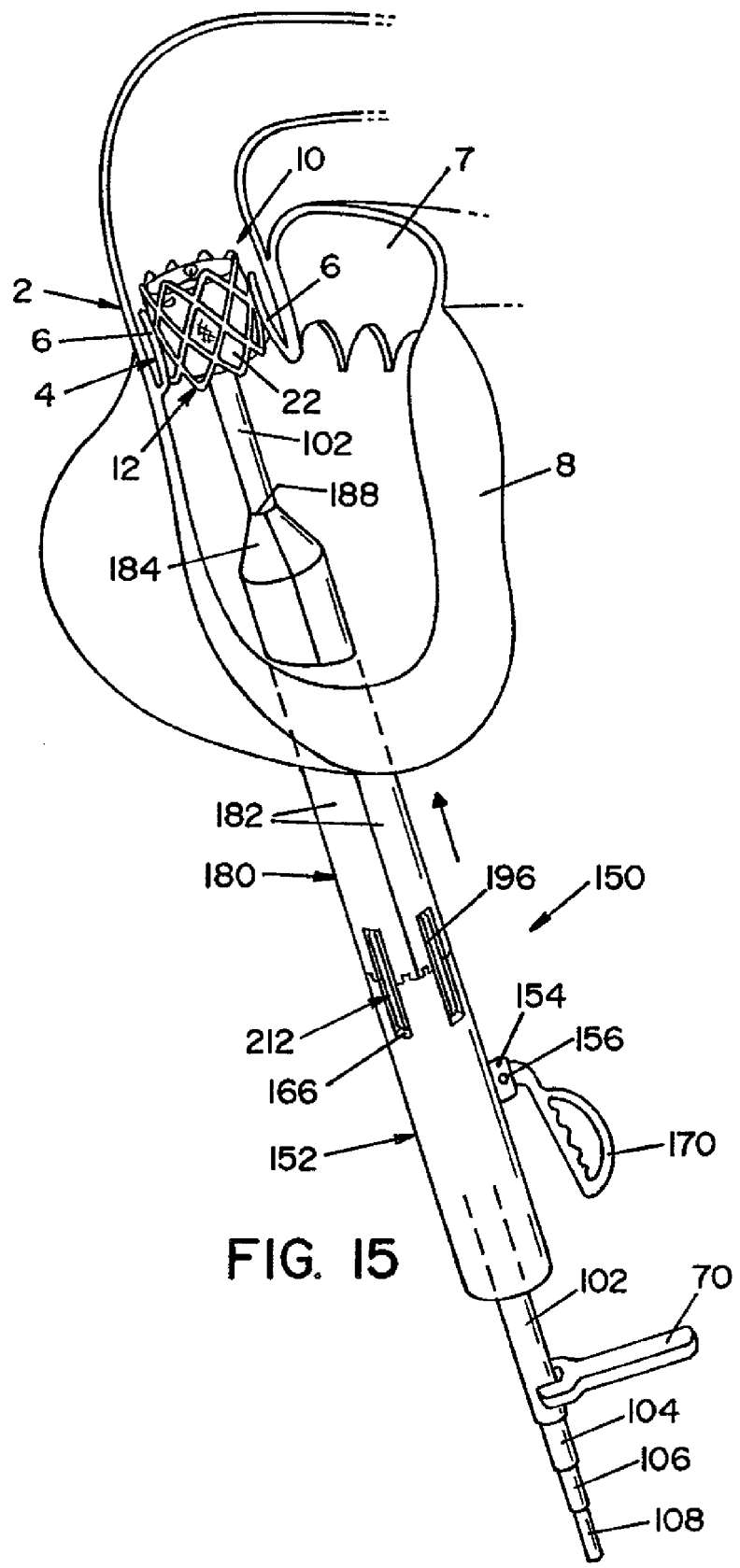
FIG. 15 is a schematic diagram showing use of a valve removal tool of the present invention for extracting the PIV from the heart, wherein the valve removal tool is inserted into the heart through the apex after removal of the cutting tool, said removal tool facilitating collapse and extraction of the PIV.

FIG. 15 schematically illustrates a valve removal tool 150, according to a first embodiment. After removal of cutting tool 120, valve removal tool 150 is slid over the stem portion of holding tool 40A and inserted into the heart through the apex. Operation of removal tool 150 will be described in detail below.

Figure 16:
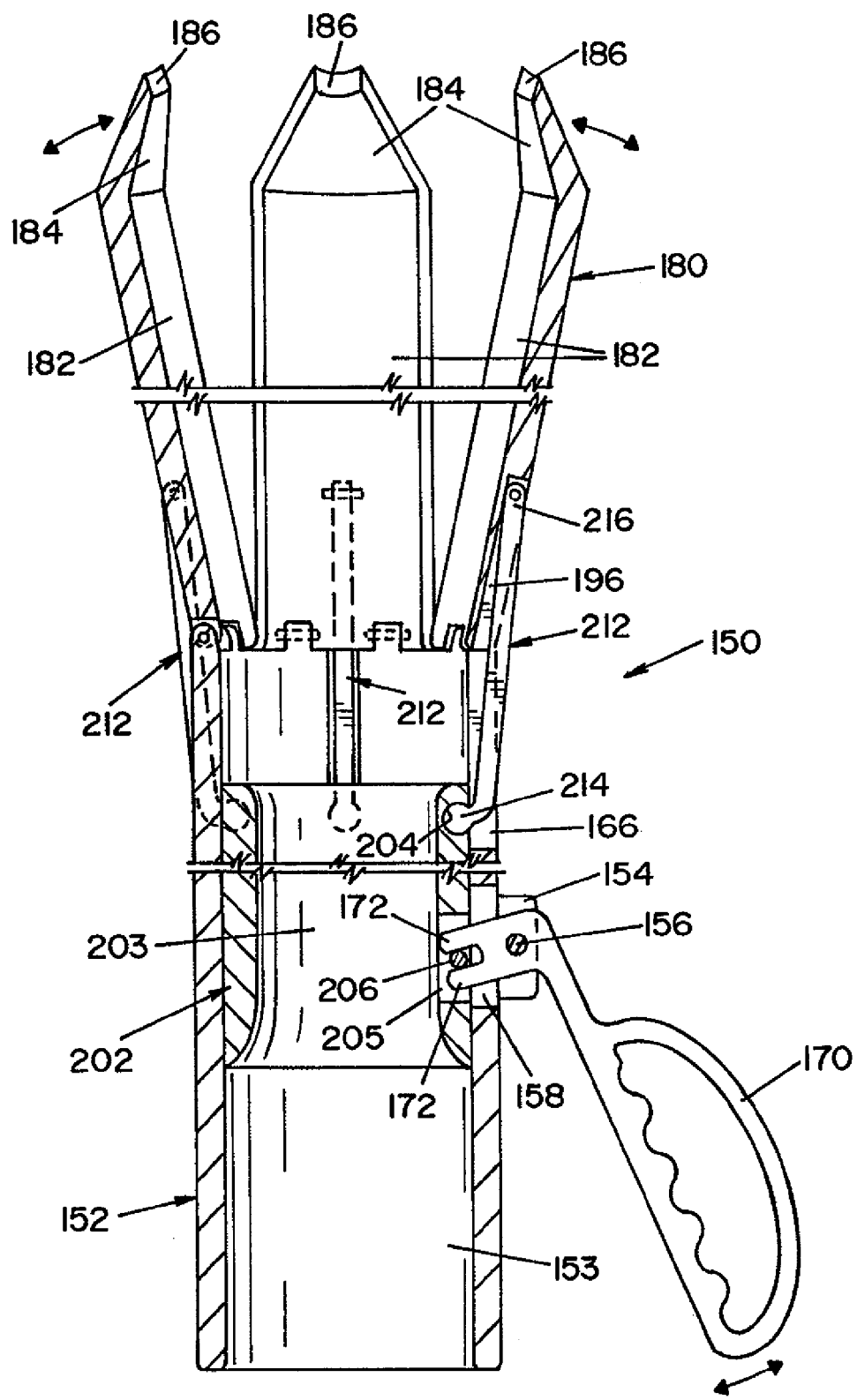
FIG. 16 is a partial cross-sectional view of the valve removal tool of FIG. 15, shown with articulating arms in an expanded (open) position.

Removal tool 150 will now be described in detail with reference to FIG. 16. Removal tool 150 resembles a trocar, and is generally comprised of a hollow cylindrical body 152, a plurality of articulating arms 180, a cylindrical inner sleeve 202, a plurality of links 212 for connecting arms 180 to inner sleeve 202, and an actuator 170 for controlling movement of arms 180.

Inner sleeve 202 is located inside a cylindrical recess 153 of cylindrical body 152. Axial movement of inner sleeve 202 within cylindrical body 152 results in movement of arms 180 between a collapsed (closed) position (FIGS. 15 and 19) and an expanded (open) position (FIG. 16). Inner sleeve 202 is connected with arms 180 via links 212. The first end 214 of link 212 has a ball hinge that is dimensioned to be received by a generally spherical cavity 204 formed in inner sleeve 202. The second end 216 of link 212 is pivotally connected to arm 180. Link 212 extends through a slot 166 in cylindrical body 152 to connect with inner sleeve 202. Inner sleeve 202 also includes a slot 205 and a pin 206. Pin 206 extends across slot 205 to operatively connect inner sleeve 202 with actuator 170. A generally cylindrical recess 203 is defined by inner sleeve 202.

A bracket member 154 extends outward from the outer surface of cylindrical body 152. Bracket member 154 supports actuator 170 that is pivotally attached to bracket member 154 by a pivot pin 156. Actuator 170 includes fingers 172 that extend through a slot 158 formed in body 152A. Fingers 172 capture pin 206 of inner sleeve 202. Rotation of actuator 170 causes axial movement of inner sleeve 202, thereby moving arms 180 between the collapsed and expanded position. In the illustrated embodiment, actuator 170 resembles a scissors handle.

Each arm 180 includes a curved elongated section 182, and an inward facing conical portion 184. A curved notch 186 is formed at the distal end of conical portion 184. When arms 180 are in the collapsed position, curved notches 186 define an opening 188. Opening 188 and cylindrical recesses 153, 203 have diameters dimensioned to receive the stem portion of holding tools 40, 40A (see FIG. 15). Each arm 180 also includes a slot 196 dimensioned to receive a portion of link 212.

Figure 17:
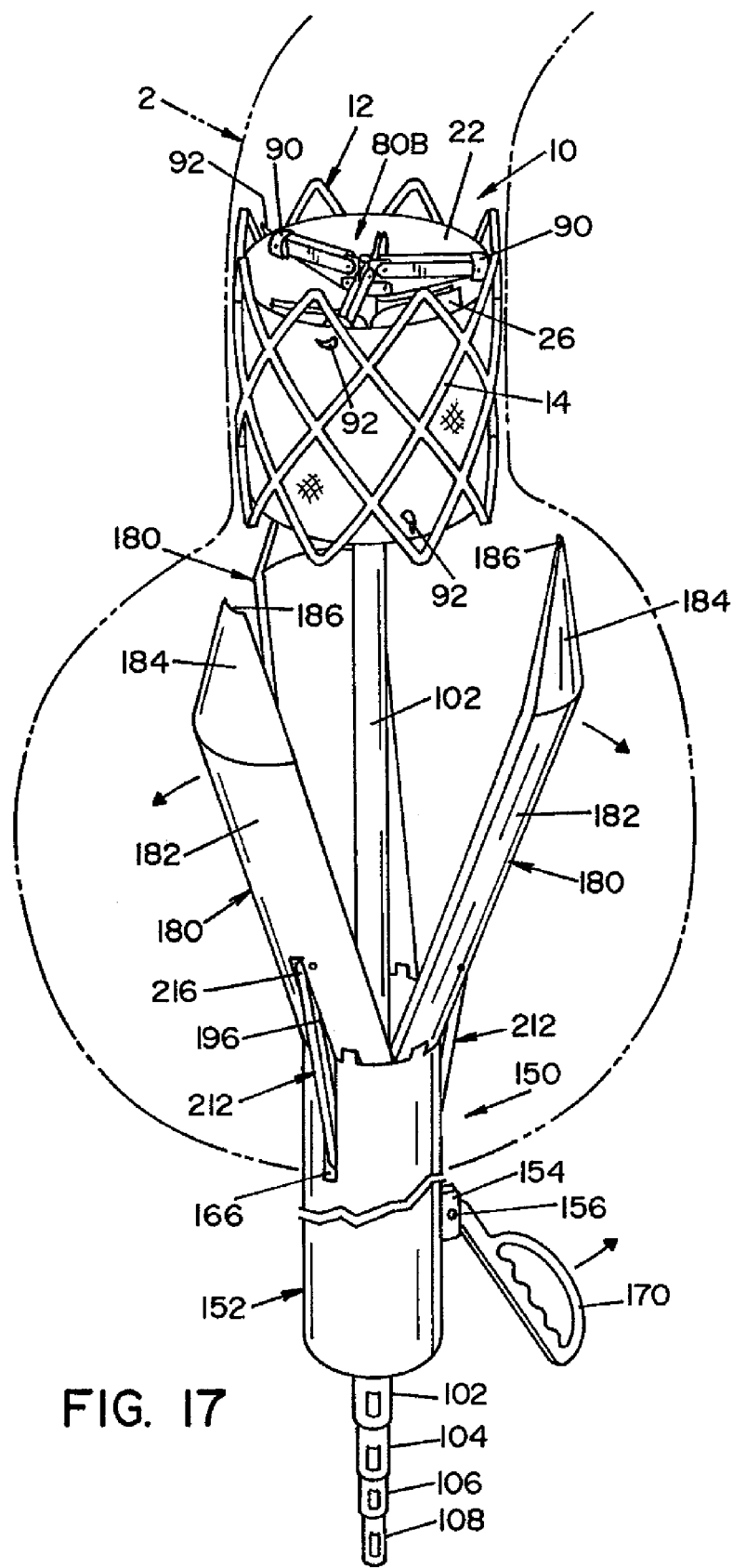
FIG. 17 is a perspective view showing the valve holding tool of FIG. 7 engaged with a PIV located inside the aortic valve, and the valve removal tool of FIGS. 15 and 16 mounted over a stem portion of the valve holding tool, shown with articulating arms in an expanded (open) position.
Figure 18:
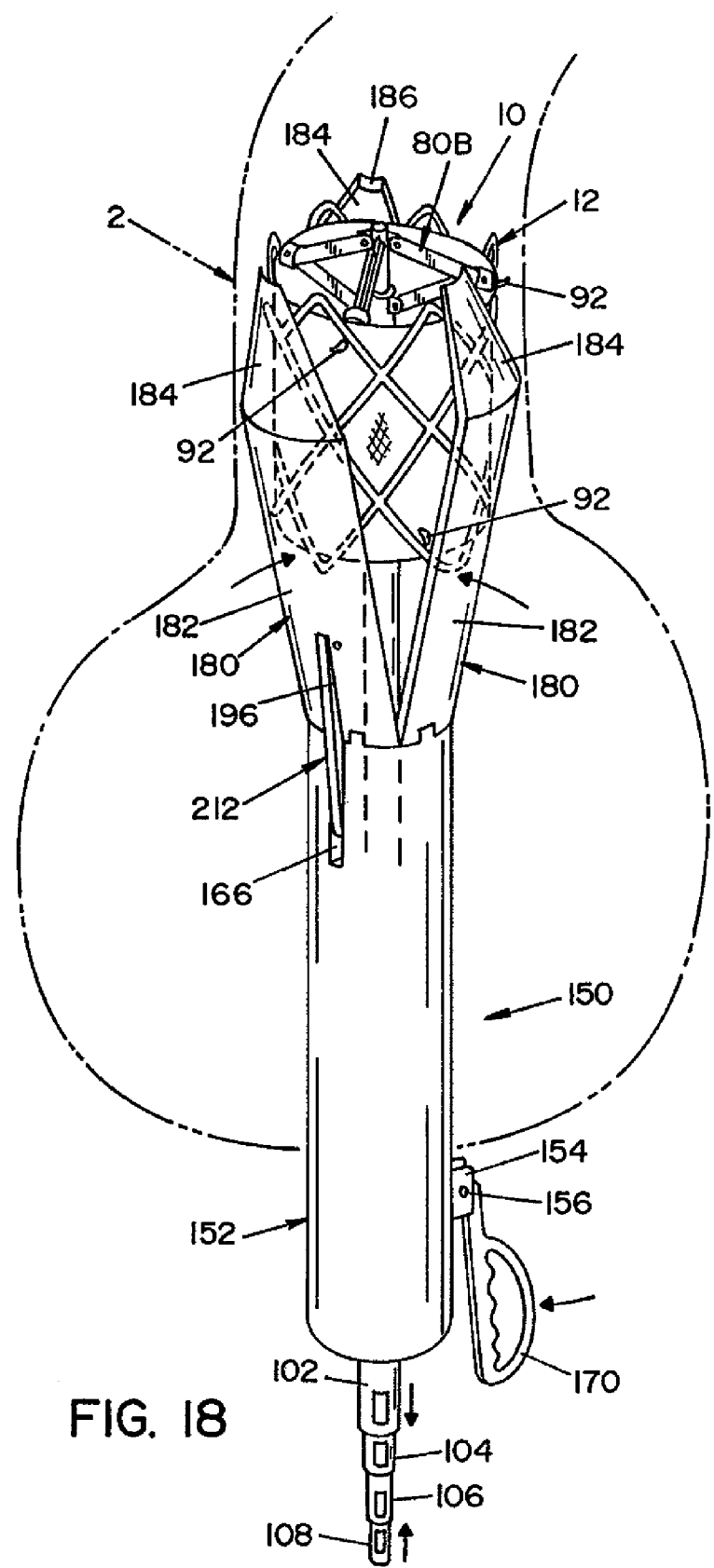
FIG. 18 is a perspective view of the valve removal tool, shown with articulating arms in a partially collapsed position for capturing the PIV.
Figure 19:
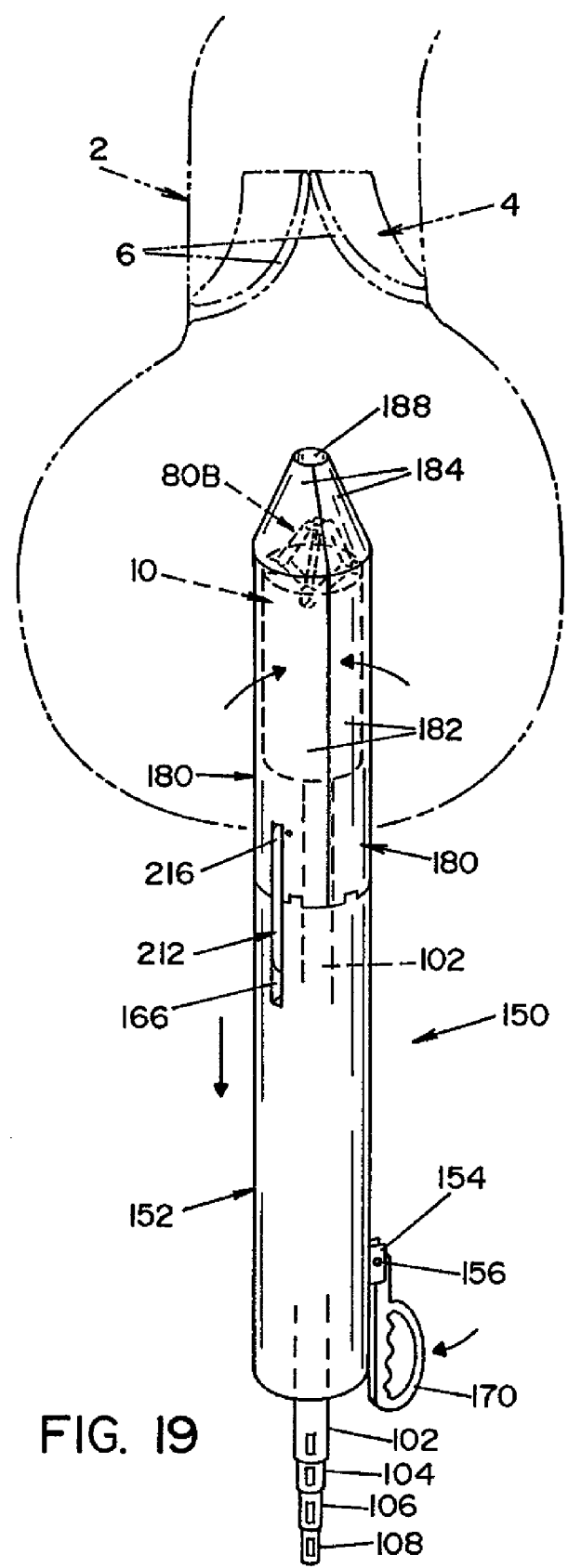
FIG. 19 is a perspective view of the valve removal tool, shown with articulating arms in a collapsed (closed) position, thereby capturing the PIV.

The operation of removal tool 150 will now be described with reference to FIGS. 15 and 17-19. Arms 180 are moved to a collapsed position and removal tool 150 is mounted over the stem portion of holding tool 40A. Removal tool 150 is inserted into the heart through the apex (FIG. 15) and moved toward PIV 10. As removal tool 150 approaches PIV 10, arms 180 are moved to the expanded position (FIG. 17). Removal tool 150 is then moved to a position relative to PIV 10 such that arms 180 can capture PIV 10 as arms 180 are moved towards collapsed position, as shown in FIG. 18. As arms 180 move to the collapsed position they exert a force on tubular member 12 of PIV 10, thereby causing tubular member 12 to collapse. In the illustrated embodiment, PIV 10 is fully captured within arms 180 when arms 180 are in the fully collapsed position shown in FIG. 19. The PIV 10 is then removed from the heart by simultaneously withdrawing both holding tool 40A and removal tool 150 from the heart, as illustrated in FIG. 19.

Figure 20:
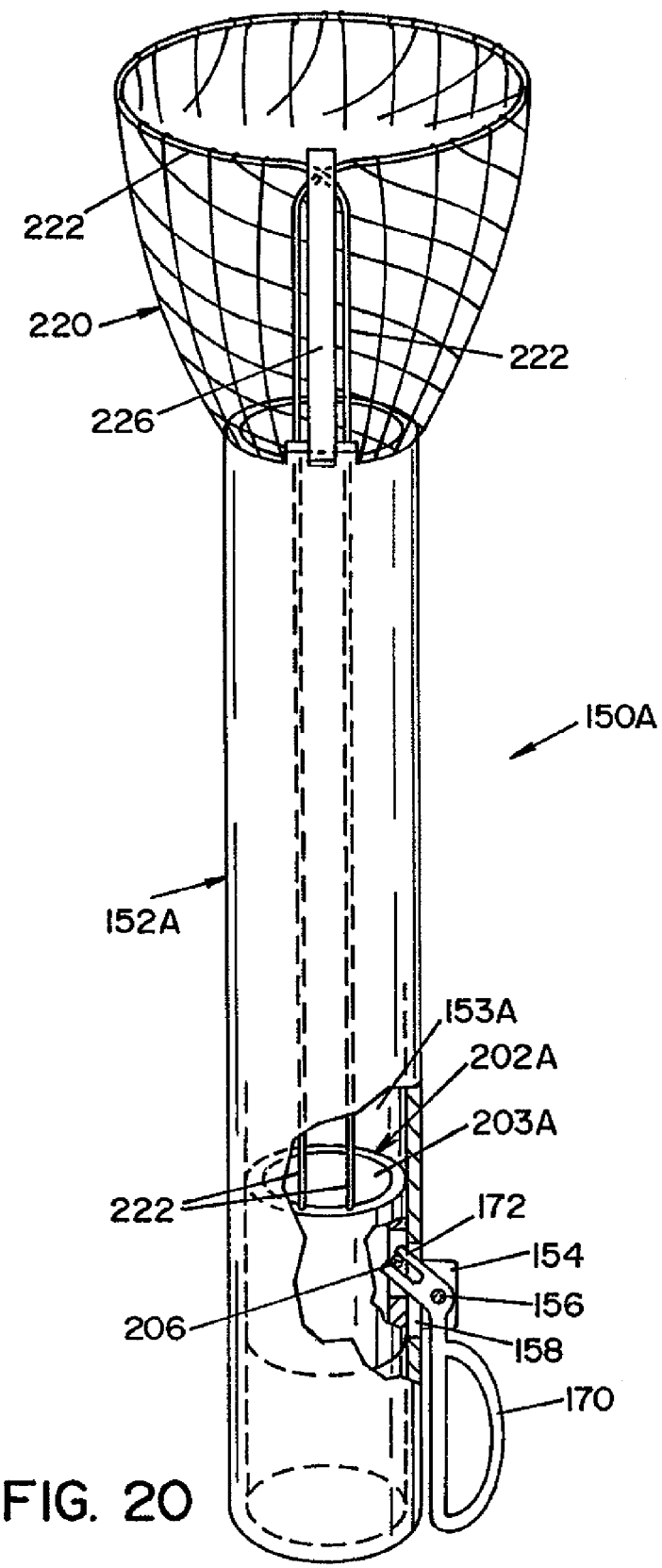
FIG. 20 is a removal tool of the present invention, according to an alternative embodiment, wherein a wire mesh basket is substituted for articulating arms, the removal tool shown in an expanded (open) position.
Figure 21:
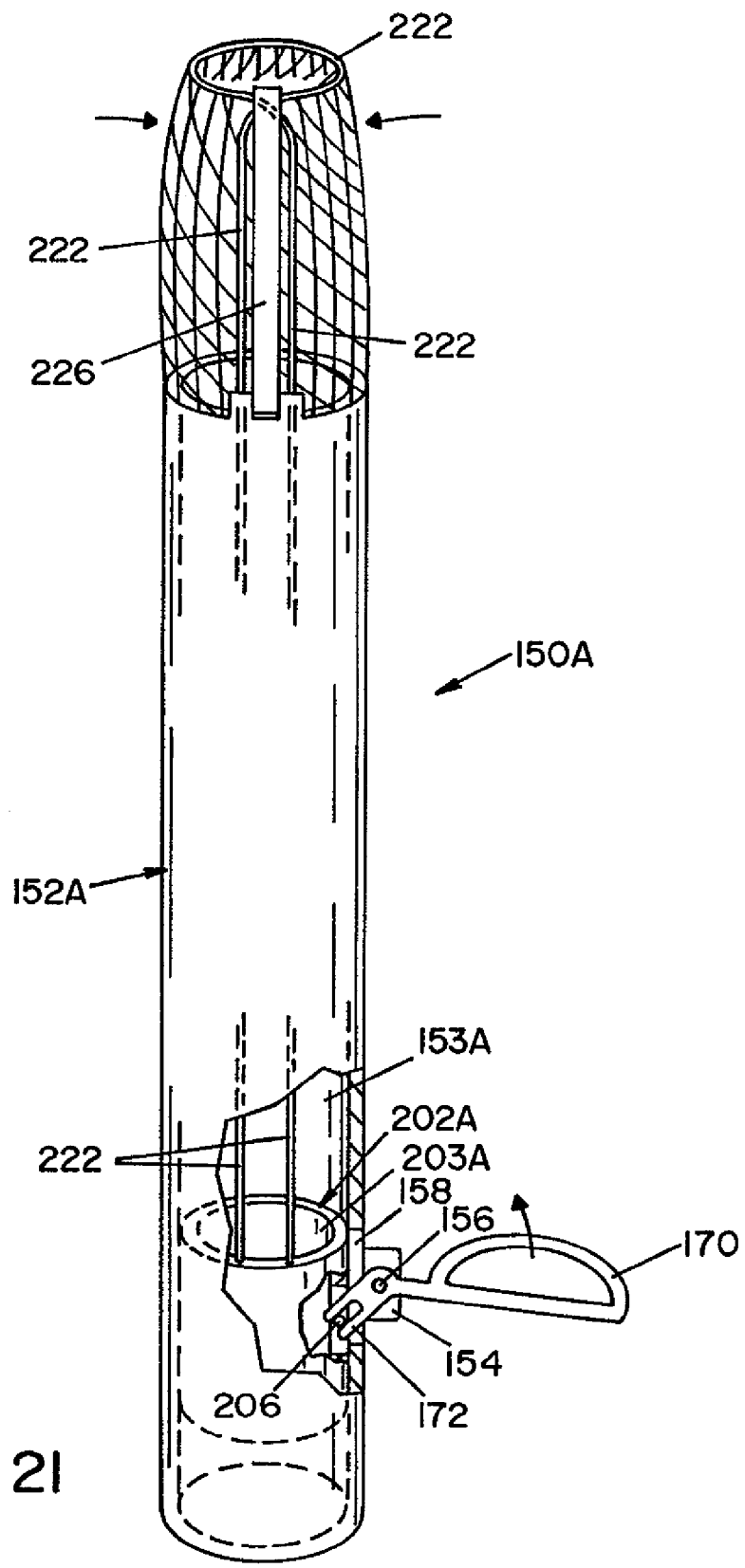
FIG. 21 is the removal tool of FIG. 19 shown in a collapsed (closed) position.

Referring now to FIGS. 20 and 21, there is shown a removal tool 150A of the present invention, according to a second embodiment. Removal tool 150A includes some of the same components as removal tool 150, and such components are labeled with the same reference numbers.

Removal tool 150A is generally comprised of a cylindrical body 152A, a cylindrical inner sleeve 202A located within a cylindrical recess 153A defined by cylindrical body 152A, and a conically-shaped wire mesh basket 220. A pivoting arm 226 extends outward from one end cylindrical body 152A. Inner sleeve 202A defines a cylindrical recess 203A.

Wire mesh basket 220 is mounted to one end of cylindrical body 152A. Wire mesh basket 220 includes a wire cable 222 that extends through a hole formed in pivoting arm 226 and connects with inner sleeve 202A. Basket 220 is dimensioned to receive PIV 10 when basket 220 is in an expanded (open) position, as shown in FIG. 20.

A bracket member 154 extends outward from the outer surface of cylindrical body 152A. Bracket member 154 supports actuator 170 that is pivotally attached to bracket member 154 by a pivot pin 156. Actuator 170 includes fingers 172 that extend through a slot 158 formed in body 152A. Fingers 172 capture pin 206 of inner sleeve 202A. Rotation of actuator 170 causes axial movement of inner sleeve 202A, thereby causing movement of wire cable 222. Application of tension to wire cable 222 moves wire mesh basket 220 from an expanded (open) position (FIG. 20) to a collapsed (closed) position (FIG. 21).

Removal tool 150A operates in a similar manner as removal tool 150 to extract PIV 10 from a heart. In this respect, removal tool 150A is adapted to be mounted over the stem portion of a holding tool, and located proximate to a PIV 10. Wire mesh basket 220 is moved between an expanded position and a collapsed position to capture and extract PIV 10.

The foregoing description is a specific embodiment of the present invention. It should be appreciated that this embodiment is described for purposes of illustration only, and that numerous alterations and modifications may be practiced by those skilled in the art without departing from the spirit and scope of the invention. For instance, it is contemplated by the inventor that the present invention may find utility with implantable cardiovascular valves other than PIVs. It is intended that all such modifications and alterations be included insofar as they come within the scope of the invention as claimed or the equivalents thereof.

Having described the invention, the following is claimed:

1. A set of tools for facilitating removal of an implanted cardiovascular valve, the set of tools comprising:
   (a) a holding tool for holding the implanted cardiovascular valve, said holding tool including:
   a first sliding member;
   a second sliding member moveable relative to the first sliding member; and
   a first member moveable between a collapsed position and an expanded position, wherein movement of the second sliding member relative to the first sliding member moves the first member between the collapsed and expanded positions, said first member engageable with the implanted cardiovascular valve in the expanded position;

(b) a cutting tool including:

a hollow shaft having a longitudinal axis and defining a recess dimensioned to mount over said first and second sliding members of the holding tool, wherein said holding tool locates the cutting tool relative to the implanted cardiovascular valve; and a cutting arm extending radially from the shaft, wherein said cutting arm includes cutting means for cutting tissue surrounding the implantable cardiovascular valve, said cutting tool rotatable relative to said holding tool to form a generally annular recess around the periphery of the implantable cardiovascular valve; and (c) a valve removal tool including:

a body having a recess dimensioned to mount over said first and second sliding members of the holding tool, wherein said holding tool locates the valve removal tool relative to the implanted cardiovascular valve;

capture means mounted to the body and moveable between a collapsed position and an expanded position, for capturing the implanted cardiovascular valve; and an actuator for actuating movement of the capture means between the collapsed and expanded positions.

2. A set of tools according to claim 1, wherein said first member is a first articulating joint member connected to the first and second sliding members.

3. A set of tools according to claim 2, wherein said first articulating joint member of the holding tool is comprised of:
a plurality of articulating legs, each of said legs including a projection for engagement with the implanted cardiovascular valve.

4. A set of tools according to claim 1, wherein said holding tool further comprises a detachable handle attachable to said first sliding member.

5. A set of tools according to claim 1, wherein said holding tool further comprises a detachable handle attachable to said second sliding member.

6. A set of tools according to claim 1, wherein said holding tool further comprises:
a third sliding member;
a fourth sliding member moveable relative to the third sliding member; and
a second member moveable between a collapsed position and an expanded position, wherein movement of the fourth sliding member relative to the third sliding member moves the second member between the collapsed and expanded positions.

7. A set of tools according to claim 6, wherein said second member is a second articulating joint member connected to the third and fourth sliding members.

8. A set of tools according to claim 7, wherein said second articulating joint member of the holding tool is comprised of:
a plurality of articulating legs, each of said legs including a projection dimensioned to engage with the implanted cardiovascular valve.

9. A set of tools according to claim 1, wherein said cutting means includes:
at least one axially-mounted fiber optic guide for projecting a laser beam in a direction generally parallel to the longitudinal axis of the shaft, said at least one axially-mounted fiber optic guide is positioned to cut a channel adjacent to the implanted cardiovascular valve.

10. A set of tools according to claim 1, wherein said cutting means includes:
at least one transverse-mounted fiber optic guide for projecting a laser beam in a direction transverse to the longitudinal axis of the shaft, said at least one transverse-mounted fiber optic guide is positioned to cut the generally annular recess around the periphery of the implanted cardiovascular valve.

11. A set of tools according to claim 1, wherein said cutting means includes a source of laser energy that is transmitted via a fiber optic cable.

12. A set of tools according to claim 1, wherein said cutting means includes a mechanical cutting device.

13. A set of tools according to claim 1, wherein said cutting means includes an electrosurgical cutting device.

14. A set of tools according to claim 1, wherein the recess of said cutting tool is dimensioned to receive a stem portion of said holding tool.

15. A set of tools according to claim 1, wherein said cutting tool further comprises a handle portion for maneuvering said cutting tool.

16. A set of tools according to claim 1, wherein said capture means of said valve removal tool includes a plurality of articulating amts.

17. A set of tools according to claim 16, wherein said actuator moves an inner sleeve relative to said body in order to effect movement of said articulating arms between the collapsed and expanded positions.

18. A set of tools according to claim 1, wherein said capture means of said valve removal tool includes a wire mesh basket.

19. A set of tools according to claim 18, wherein said actuator applies tension to the wire mesh basket in order to effect movement of said wire mesh basket to the collapsed position.

20. A set of tools according to claim 18, wherein the recess of said body is dimensioned to receive a stem portion of said holding tool.

* * * * *